United States Patent
Hanashi et al.

(10) Patent No.: US 9,435,727 B2
(45) Date of Patent: Sep. 6, 2016

(54) OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

(71) Applicant: OLYMPUS CORPORATION, Tokyo (JP)

(72) Inventors: Takuya Hanashi, Hachioji (JP); Mitsushiro Yamaguchi, Hachioji (JP); Tetsuya Tanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 53 days.

(21) Appl. No.: 13/969,830

(22) Filed: Aug. 19, 2013

(65) Prior Publication Data

US 2013/0338968 A1 Dec. 19, 2013

Related U.S. Application Data

(63) Continuation of application No. PCT/JP2012/057731, filed on Mar. 26, 2012.

(30) Foreign Application Priority Data

Mar. 29, 2011 (JP) .................................. 2011-071545

(51) Int. Cl.
*G01N 15/14* (2006.01)
*G01N 21/64* (2006.01)
(Continued)

(52) U.S. Cl.
CPC .......... *G01N 15/1429* (2013.01); *G01N 21/51* (2013.01); *G01N 21/645* (2013.01);
(Continued)

(58) Field of Classification Search
CPC .................... G01N 21/6458; G01N 21/6486; G01N 21/6456; G01N 21/6452; G01N 21/6408; G01N 21/6404; G01N 21/6402; G01N 21/64; G01N 21/76; G01N 21/763; G01N 21/0303; G01N 2201/1087; G01N 2201/103; G01N 15/14; G01N 15/1463; G01N 2015/1486; G02B 21/00; G02B 21/002; G02B 21/0024; G02B 21/0032; G02B 21/0076; G02B 21/06; G02B 21/16; G02B 25/02
See application file for complete search history.

(56) References Cited

U.S. PATENT DOCUMENTS

| | | |
|---|---|---|
| 4,251,733 A | 2/1981 | Hirleman, Jr. |
| 5,866,336 A | 2/1999 | Nazarenko et al. |

(Continued)

FOREIGN PATENT DOCUMENTS

| | | |
|---|---|---|
| EP | 1 906 172 A1 | 4/2008 |
| JP | 04-337446 A | 11/1992 |

(Continued)

OTHER PUBLICATIONS

Steffen Ruttinger, Confocal Microscopy and Quantitative Single Molecule Techniques for Metrology in Molecular Medicine, 2006, Dissertation, Technical University Berlin, 155 pp.*

(Continued)

*Primary Examiner* — Toan Le

(74) *Attorney, Agent, or Firm* — Westerman, Hattori, Daniels & Adrian, LLP

(57) ABSTRACT

There is provided a structure to make the setting of a criterion for eliminating noises easy in the scanning molecule counting method. In the inventive optical analysis technique of detecting light of a light-emitting particle in a sample solution, time series light intensity data of light from a light detection region detected with moving the position of the light detection region in the sample solution is generated, and a signal of a light-emitting particle individually is detected in the time series light intensity data, wherein a signal having a light intensity in a light intensity range set based upon a signal generation frequency integrated value distribution which is a distribution, obtained by using as a variable an intensity of a signal, of integrated values of generation frequencies of signals having an intensity not lower than the variable is extracted as the signal of the light-emitting particle.

21 Claims, 8 Drawing Sheets

Figures 1A, 1B, 1C:
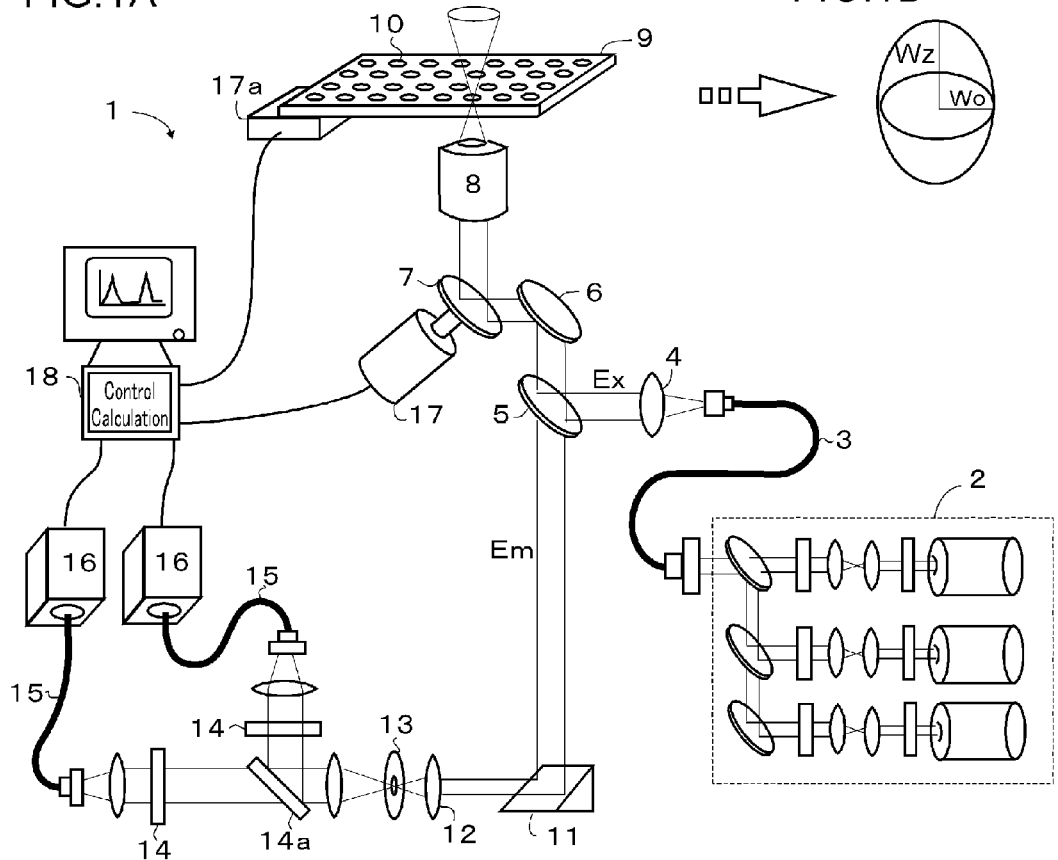

(51) Int. Cl.
*G01N 21/51* (2006.01)
*G02B 21/00* (2006.01)

(52) U.S. Cl.
CPC ...... *G01N21/6408* (2013.01); *G01N 21/6458* (2013.01); *G02B 21/0076* (2013.01); *G02B 21/0084* (2013.01)

(56) References Cited

U.S. PATENT DOCUMENTS

| | | |
|---|---|---|
| 6,280,960 B1 | 8/2001 | Carr |
| 6,376,843 B1 | 4/2002 | Palo |
| 6,388,746 B1 | 5/2002 | Eriksson et al. |
| 6,388,788 B1 | 5/2002 | Harris et al. |
| 6,400,487 B1 | 6/2002 | Harris et al. |
| 6,403,338 B1 | 6/2002 | Knapp et al. |
| 6,710,871 B1 | 3/2004 | Goix |
| 6,782,297 B2 | 8/2004 | Tabor |
| 6,856,391 B2 | 2/2005 | Garab et al. |
| 6,927,401 B1 | 8/2005 | Palo |
| 8,284,484 B2 | 10/2012 | Hoult et al. |
| 2001/0035954 A1 | 11/2001 | Rahn et al. |
| 2002/0008211 A1 | 1/2002 | Kask |
| 2002/0036775 A1 | 3/2002 | Wolleschensky et al. |
| 2003/0036855 A1 | 2/2003 | Harris et al. |
| 2003/0218746 A1 | 11/2003 | Sampas |
| 2004/0022684 A1 | 2/2004 | Heinze et al. |
| 2004/0051051 A1 | 3/2004 | Kato et al. |
| 2004/0150880 A1 | 8/2004 | Nakata et al. |
| 2005/0260660 A1 | 11/2005 | van Dongen et al. |
| 2006/0078998 A1 | 4/2006 | Puskas et al. |
| 2006/0158721 A1 | 7/2006 | Nakata et al. |
| 2006/0256338 A1 | 11/2006 | Gratton et al. |
| 2008/0021674 A1 | 1/2008 | Puskas |
| 2008/0052009 A1 | 2/2008 | Chiu et al. |
| 2008/0117421 A1 | 5/2008 | Yamaguchi et al. |
| 2009/0159812 A1 | 6/2009 | Livingston |
| 2010/0033718 A1 | 2/2010 | Tanaami |
| 2010/0177190 A1 | 7/2010 | Chiang et al. |
| 2010/0202043 A1 | 8/2010 | Ujike |

FOREIGN PATENT DOCUMENTS

| | | |
|---|---|---|
| JP | 10-512952 A | 12/1998 |
| JP | 2002-507762 A | 3/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-017127 A | 1/2010 |
| JP | 2010-190730 A | 9/2010 |
| JP | 2011-002415 A | 1/2011 |
| JP | 2011-508219 A | 3/2011 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |
| WO | 2012/032955 A1 | 3/2012 |
| WO | 2012/032981 A1 | 3/2012 |
| WO | 2012/039352 A1 | 3/2012 |

OTHER PUBLICATIONS

Zheng et al., Homebuilt Single-Molecule Scanning Confocal Fluorescence Microscope Studies of Single DNA/Protein Interactions, Mar. 2007, NIH Public Access, 22 pp.*
Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, p. 1612-1618.
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report Mar. 29, 2011, issued in related PCT/JP2011/053482.
International Preliminary Report on Patentability (PCT/IPEA/409) issued in related PCT/JP2011/053482.
U.S. Office Action dated Jan. 3, 2013, issued in related U.S. Appl. No. 13/597,825.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry," Nucleic Acids Research, 1993, vol. 21, No. 4, p. 803-806.
Keller, Richard et al., "Single-Molecule Fluorescence Analysis in Solution," Applied Spectroscopy, 1996, vol. 50, No. 7, p. 12A-32A.
Lee, Yuan-Hsiang et al., "Laser-Induced Fluorescence Detection of a Single Molecule in a Capillary," Analytical Chemistry, dated Dec. 1, 1994, vol. 66, No. 23, p. 4142-4149.
Li, Haitao et al., "Ultrasensitive Coincidence Fluorescence Detection of Single DNA Molecules," Analytical Chemistry, dated Apr. 1, 2003, vol. 75, No. 7, p. 1664-1670.
Nie, Shuming et al., "Probing Individual Molecules with Confocal Fluorescence Microscopy," Science, dated Nov. 11, 1994, vol. 266, p. 1018-1021.
Tahari, Abdel. "Fluorescence Correlation Spectroscopy: Ultrasensitive Detection in Clear and Turbid Media," University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy," Chemistry and Biology, 2009, vol. 47, No. 12, p. 823-830.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.

(56) References Cited

OTHER PUBLICATIONS

U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
International Search Report dated Nov. 29, 2011, issued in related PCT/JP2011/071196.
Guo, Xiang-Qun et al., "Use of a Long-Lifetime Re(I) Complex in Fluorescence Polarization Immunoassays of High-Molecular-Weight Analytes", Analytical Chemistry, Feb. 1998, vol. 7, No. 3, p. 632-637.
International Search Report dated Jun. 26, 2012, issued in related PCT/JP2012/058840.
International Search Report dated Aug. 14, 2012, issued in related PCT/JP2012/066943.
International Search Report dated Mar. 5, 2013, issued in related PCT/JP2013/052446.
Supplementary European Search Report dated Feb. 13, 2014, issued in related EP application No. 11826797.0.
International Search Report dated Nov. 29, 2011, issued in related PCT/JP2011/072939.
Kinjo, Masataka, "Single molecule protein, nucleic acid, and enzyme assays and their procedures; Single molecule detection by fluorescence correlation spectroscopy", Protein, Nucleic Acid, Enzyme, 1999, vol. 44, No. 9, pp. 1431-1438, cited in specification, w/ English translation.
Meyer-Almes, F.J., "Nanoparticle Immunoassays: A new Method for Use in Molecular Diagnostics and High Throughput Pharmaceutical Screening based on Fluorescence Correlation Spectroscopy", edit. R. Rigler, Springer, Berlin, 2000, pp. 204-224, cited in specification.
Kato, Noriko et al., "A single molecule analyzer that enable new analysis of DNA and protein interactions", Gene medicine, 2002, vol. 6, No. 2, pp. 271-277, cited in specification.
Kask, P. et al., "Fluorescence-intensity distribution analysis and its application in biomolecular detection technology", PNAS, Nov. 23, 1999, vol. 96, No. 24, pp. 13756-13761 Cited in Specification.
International Search Report for PCT/JP2012/057731, Mailing Date of Jun. 26, 2012.
Extended European Search Report dated Oct. 20, 2014, issued in related European Patent No. 12770835.2 (10 pages).
Office Action dated Nov. 15, 2014, issued in corresponding Chinese Patent Application No. 201280016619.0, with English Translation (11 pages).
Extended European Search Report dated Sep. 30, 2014, issued in corresponding EP application No. 12763462.4 (12 pages).
Notice of Reasons for Rejection dated Aug. 11, 2015, issued in Japanese application No. 2012-535020, with English translation. (5 pages).
Communication Pursuant to Article 94(3) EPC dated Feb. 19, 2015, issued in corresponding European Patent Application No. 11826797.0. (4 pages).
Communication dated Oct. 23, 2015, issued in EP application No. 11826797.0.
Final Office Action dated Sep. 28, 2015, issued in U.S. Appl. No. 13/746,968 (24 pages).
Final Office Action dated Sep. 29, 2015, issued in U.S. Appl. No. 13/946,091 (23 pages).

\* cited by examiner

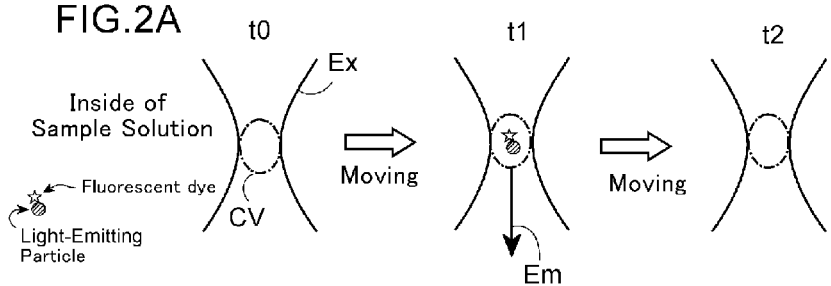
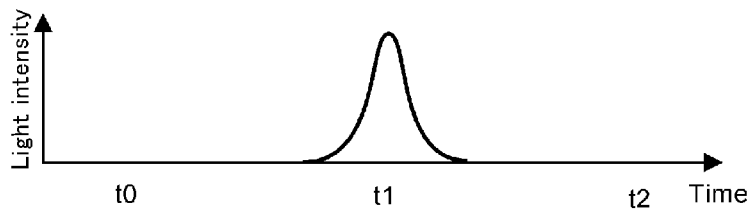
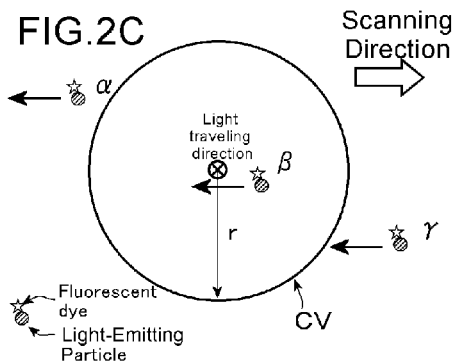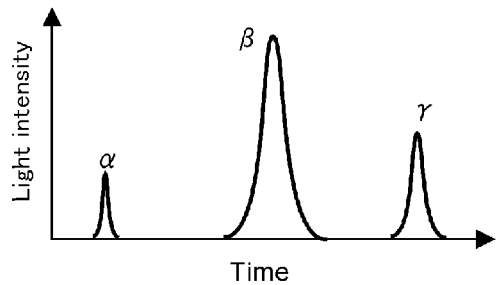
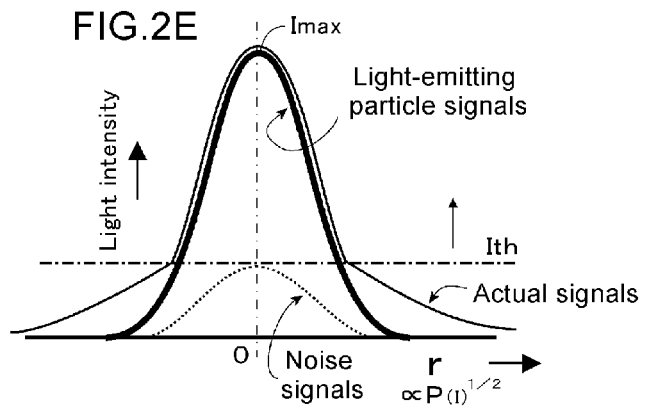

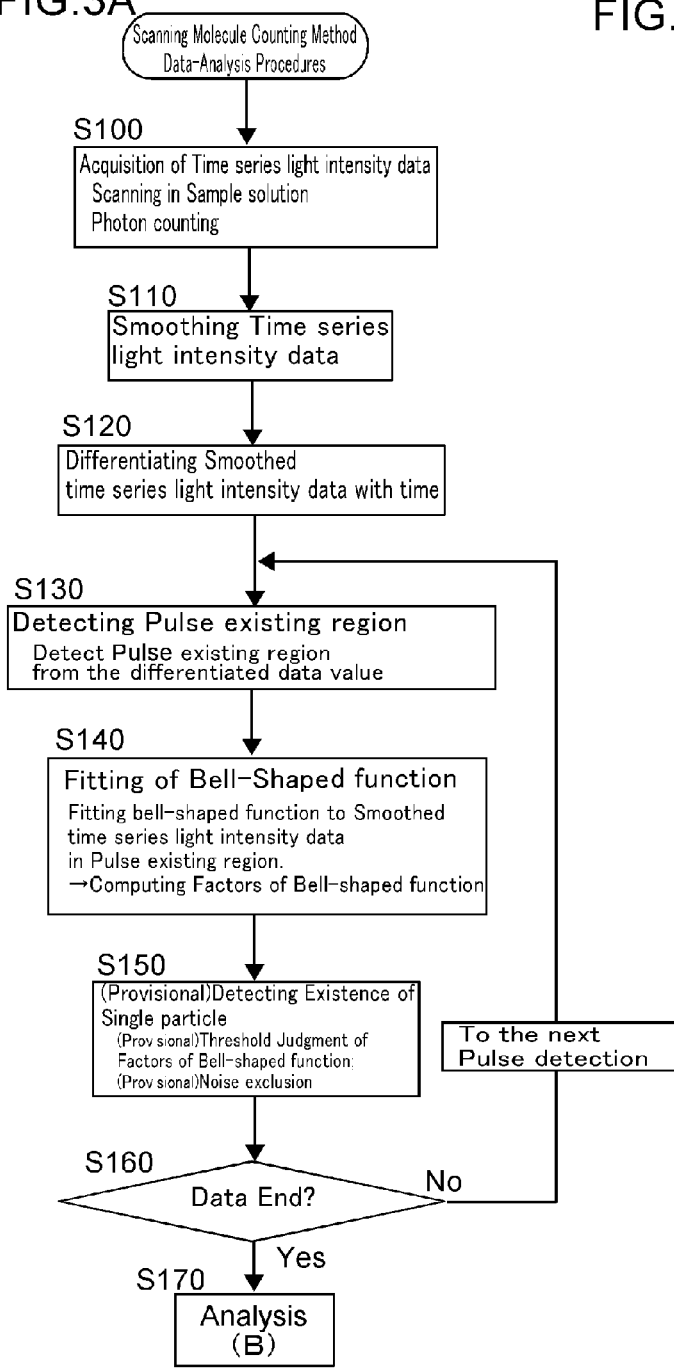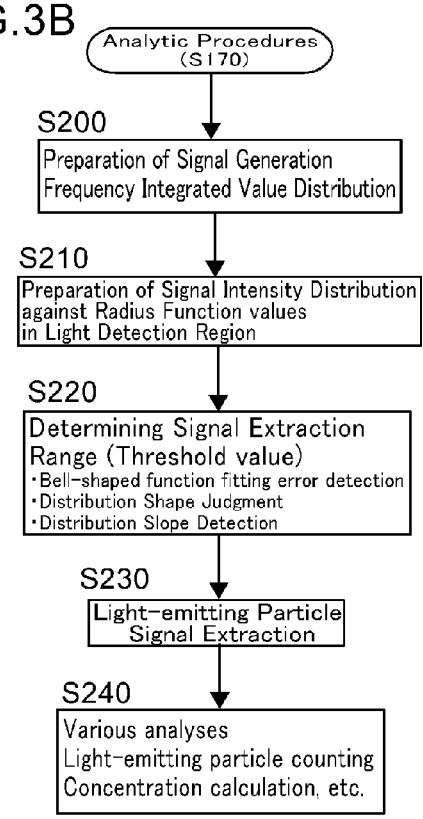

FIG.4A
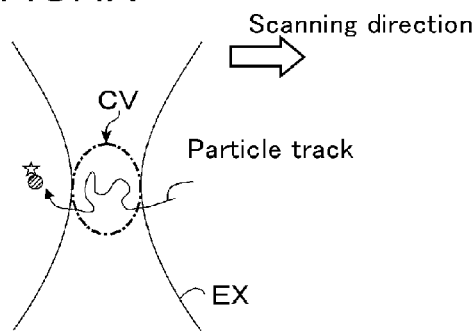
FIG.4B
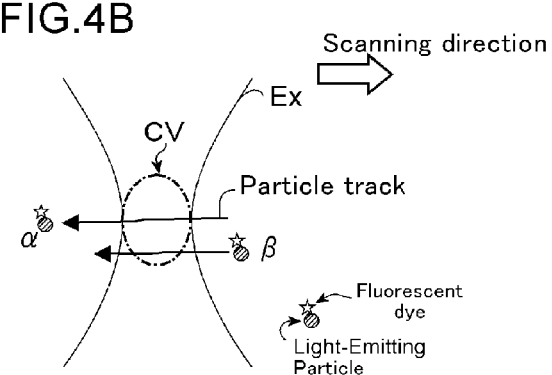
FIG.4C
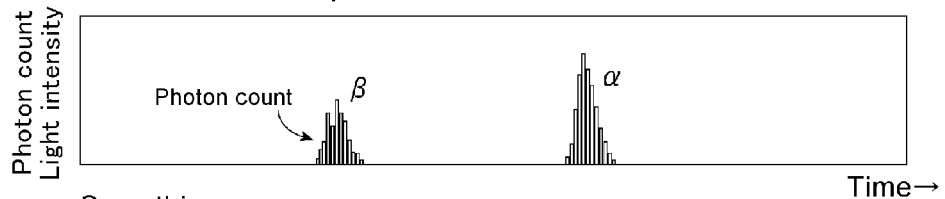
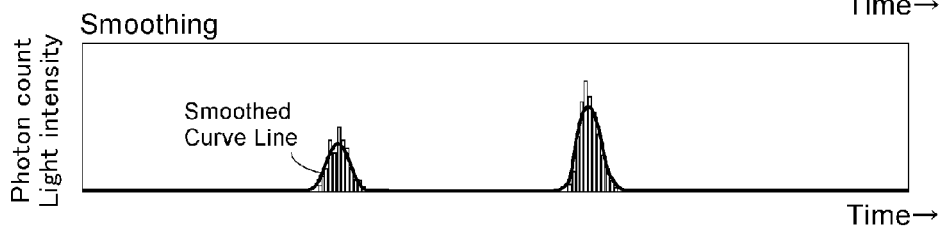
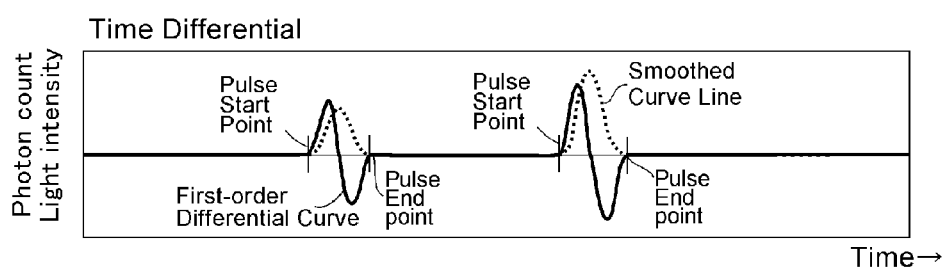
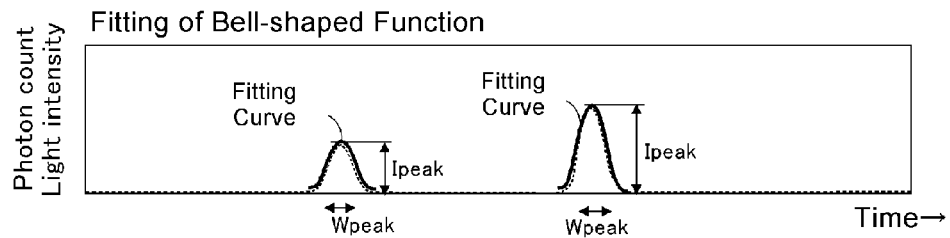

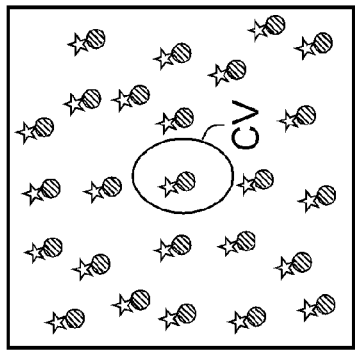
FIG.8A High Concentration (e.g. ~ 1nM)
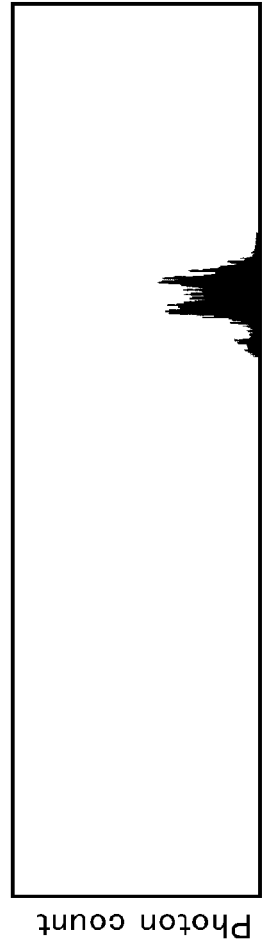
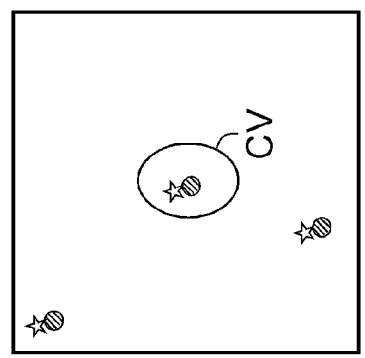
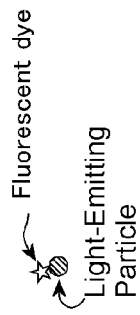
FIG.8B Low Concentration (e.g. ~ 1pM)

OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to an optical analysis device, optical analysis method and computer program for optical analysis, which detect individually the light from a single particle which emits light, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of μL), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098870
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.

Non-patent document 2: F. J. Meyer-Alms; "Fluorescence Correlation Spectroscopy" edt. R. Rigler, Springer, Berlin, pages 204-224, 2000.

Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light statistical procedures for the calculating of the fluorescence intensity fluctuation, etc., such as the computation of the autocorrelation function or the fitting to the histogram of fluorescence intensity data measured in time series, and therefore the signal of the light from individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

In the above-mentioned scanning molecule counting method, when a light intensity increase, equivalent to the light from a light-emitting particle (typically a bell shaped profile), is observed in a time series data of the light intensity values (or photon count values) measured with moving the position of a light detection region in a sample solution, it is judged that one light-emitting particle has been encompassed in the light detection region, and thereby a detection of an existence of one light-emitting particle is made. In this structure, since there exist noises (the heat noises of a photodetector, background light), other than the light from light-emitting particles, in actual time series light intensity data, it is necessary to detect an existence of a signal indicating a light from a light-emitting particle (a signal of a light-emitting particle) with eliminating noises. Thus, typically, the extraction of a signal of a light-emitting particle is tried with reference to a characteristic of the signal of the light-emitting particle, e.g., the intensity magnitude, the shape of the signal, etc. In this respect, the characteristics of signals of light-emitting particles or the magnitudes and shapes of noises vary depending upon measurement conditions (the adjustment conditions of a device and an optical system, the environmental temperature, the light-emitting characteristics of the light-emitting particles, the condition of a sample solution, etc.), and also, an explicit criterion for eliminating noises from the signals of the light-emitting particles has not been clear. So, typically, the setting of the criterion for eliminating noises has been made by trial and error through acquiring time series light intensity data of a reference solution containing a light-emitting particle to be an observation object or a particle equivalent thereto (positive control) and a reference solution containing no light-emitting particle to be an observation object or no particle equivalent thereto in each measurement condition and comparing light intensity values observed in those time series light intensity data. However, such trial and error in the setting of the criterion for eliminating noises are cumbersome and time- and labor-consuming works for a performer of the analysis.

Thus, one object of the present invention is to propose a new way of making it easier to perform the setting of a criterion or an index for detecting a signal of a light-emitting particle with eliminating noises in the scanning molecule counting method as described above.

In this regard, the inventor of the present invention has found that it is possible to determine easily a criterion for eliminating noise signals and detecting signals of light-emitting particles based upon a distribution of the generation frequencies of light intensities in time series light intensity data obtained by the scanning molecule counting method using an arbitrary sample solution under a certain measurement condition (more in detail, a distribution, obtained by using the intensity of the signal detected in time series light intensity data as its variable, of the integrated values of the generation frequencies of signals having an intensity not lower than the variable).

As described in detail later, the intensity of the light, which is emitted from a single light-emitting particle in the focal area of the optical system of a confocal microscope or multiphoton microscope used in the "scanning molecule counting method", a "light detection region" and reaches to a photodetector, varies depending upon the position of the light-emitting particle in the light detection region, and typically, when the position of the light-emitting particle is in the almost central region of the light detection region, the light intensity becomes its maximum (in the following, the position at which the light intensity of a light-emitting particle becomes the maximum in the light detection region is called the "maximum intensity point".), and the light intensity is gradually reduced as the position of the light-emitting particle approaches the circumference of the light detection region. Namely, the distribution of the light intensities, emitted from light-emitting particles in the light detection region and detected, becomes a distribution having an approximately bell-shaped profile in which the intensity reduces from the maximum intensity point toward the circumference. And the light-emitting particles are considered to be dispersed almost uniformly in the sample solution comprising the light detection region, and therefore, the distribution of the generation frequencies of the light intensities of signals of light-emitting particles is determined with the intensity distribution of the lights emitted from the light-emitting particles in the light detection region and detected, namely, the intensity distribution of lights which reach from the light detection region to a photodetector. On the other hand, noises are generated at random, and there is no dependency on the intensity distribution of lights emitted from light-emitting particles in the light detection region and detected. Thus, it can be considered that, in a distribution of the generation frequencies of the light intensities in time series light intensity data, a signal which gives a component consistent with an intensity distribution of lights emitted from light-emitting particles in the light detection region and detected is "a signal of a light-emitting particle", and signals which give the other components are "noises". Therefore, it becomes possible to detect a signal of a light-emitting particle under the condition that noise signals are eliminated with reference to whether or not a signal detected on time series light intensity data is a component consistent with an intensity distribution of lights emitted from light-emitting particles in the light detection region and detected.

In the present invention, using the above-mentioned knowledge, there is proposed a structure which determines easily a criterion for detecting a signal of a light-emitting particle with eliminating noise signals in the scanning molecule counting method.

Solution to Problem

According to one aspect of the present invention, the above-mentioned object is achieved by an optical analysis device which detects light from a light-emitting particle dispersed and moving at random in a sample solution using an optical system of a confocal microscope or a multiphoton microscope, characterized by comprising: a light detection region mover which moves a position of a light detection region of the optical system of the microscope in the sample solution by changing an optical path of the optical system; a light detector which detects light from the light detection region; and a signal processor which generates time series light intensity data of the light from the light detection region detected with the light detector with moving the position of the light detection region in the sample solution and detects a signal from each light-emitting particle individually in the time series light intensity data; wherein the signal processor detects the signal from each light-emitting particle by extracting, as the signal of the light-emitting particle from a group of signals detected in the time series light intensity data, a signal having a light intensity in a light intensity range having been set based upon a signal generation frequency integrated value distribution which is a distribution, obtained by using as a variable an intensity of a signal detected in the time series light intensity data, of integrated values of generation frequencies of signals having an intensity not lower than the variable. In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Further, in the followings in this specification, "a signal of a light-emitting particle" means "a signal expressing light from a light-emitting particle" unless noted otherwise.

As understood from the above, in the basic structure of the present invention, i.e., the scanning molecule counting method, the light detection is sequentially performed while the position of a light detection region is moved in a sample solution, namely, while the inside of the sample solution is scanned with the light detection region. Then, when the light detection region moving in the sample solution encompasses a randomly moving light-emitting particle, the light from the light-emitting particle is detected by the light detector, and thereby, it is expected that the existence of one particle will be detected. Thus, in the sequentially detected light, a signal indicating the light from a light-emitting particle is individually detected, and thereby, the individual existences of light-emitting particles are detected one by one, and accordingly, diverse information on the condition of a particle in the solution will be acquired. In that case, in the present invention, in accordance with the above-mentioned knowledge, i.e., the knowledge that the detection of a signal of a light-emitting particle with eliminating noise signals becomes easier by referring to a distribution of the generation frequencies of the light intensities in the time series light intensity data, a light intensity range of signals to be extracted as a signal of a light-emitting particle on the time series light intensity data is set based on a "signal generation frequency integrated value distribution", i.e., a distribution, obtained by using, as its variable, an intensity of a signal detected in the time series light intensity data, of the integrated values of the generation frequencies of signals having an intensity not lower than the variable. And, signals having a light intensity in the above-mentioned light intensity range are extracted from the group of the signals detected in time series light intensity data with eliminating noises, and thereby the detection of the signal from each light-emitting particle is done.

In this regard, as understood from the explanation of the section of embodiments later, a distribution of the intensities of lights emitted from light-emitting particles in the light detection region and detected against positions in the inside of the light detection region can be estimated from the signal generation frequency integrated value distribution, and it is considered that the intensity of a signal of a light-emitting particle follows the intensity distribution of the lights emitted from light-emitting particles in the light detection region and detected. Thus, preferably, the above-mentioned light intensity range for a signal to be extracted as a signal of a light-emitting particle may be a light intensity range in which the intensity distribution of signals against positions in the inside of the light detection region, determined based on a signal generation frequency integrated value distribution, substantially accords with an intensity distribution of lights emitted from light-emitting particles in the light detection region and detected. (Here, "substantially accords with" means that the difference within the limits of an allowable error is permitted.)

Further, as already noted, typically, the intensity distribution of lights emitted from light-emitting particles in the light detection region and detected is a distribution having a bell shaped profile in which the light intensity reduces as the position of a light-emitting particle approaches the circumference of the light detection region from the maximum intensity point, and the intensity distribution of the signals of light-emitting particles is also considered to have a similar bell shaped profile (Especially in a case that light-emitting particles are particles emitting light by irradiation of excitation light and the light detection region is defined with the condensing region of the excitation light, the intensity distribution of lights emitted from light-emitting particles in the light detection region and detected is in agreement with the intensity distribution of the excitation light in the light detection region.). And the signals of light-emitting particles which can actually be observed are those of particles having a larger intensity than the intensity of noises (If the bell shaped profile of the intensity distribution of the signals of light-emitting particles is buried in the noise intensity, no observation of signals of light-emitting particles can be performed primarily.). Thus, in the above-mentioned inventive structure, the signal processor may be designed to set a threshold value as the limit of the light intensity range set based on the signal generation frequency integrated value distribution, and extract a signal having an intensity beyond the threshold value on the time series light intensity data as a signal of a light-emitting particle. Preferably, the threshold value may be set to the upper limit of the noise intensity in time series light intensity data.

In the setting of the light intensity range for a signal to be extracted as a signal of a light-emitting particle in the above-mentioned inventive device, in more detail, for example, after determining an intensity distribution of signals against function values of positions in the inside of the light detection region determined based on the signal generation frequency integrated value distribution, the fitting of a bell type function, such as a Gauss function and a Lorentz function, may be carried out to the intensity distribution of the signals against function values of positions in the inside of the light detection region. Here, "function values of the positions in the inside of the light detection region" may be, for instance, the radii from the maximum intensity point in the light detection region or their function values. (As explained in the below-mentioned section of embodiments, an integrated value, obtained by using, as its variable, an intensity of a signal on time series light intensity data, of the generation frequencies of signals of light-emitting particles having an intensity beyond the variable can be represented as a function of the position of inside of the light detection region, e.g. the radius from the maximum intensity point). As already noted, an intensity distribution of lights emitted from light-emitting particles in the light detection region and detected has a bell shaped profile, and thus, its good fitting with a bell type function is possible. Accordingly, in the intensity distribution of signals, it is considered that, in a site or region where the fitting error in the fitting with a bell type function is large, the influence of noises is large, and therefore, with reference to the above-mentioned fitting error, the light intensity range for the signal to be extracted as a signal of a light-emitting particle can be set based on that error.

Furthermore, as understood from the explanation in the section of embodiments later, by referring to the shape of a distribution of the intensities of signals against function values of positions in the light detection region, determined based on the signal generation frequency integrated value distribution, or the shape of the signal generation frequency integrated value distribution itself, it is possible to judge the region where the deviation in the shape of the distribution from the bell shaped profile of the intensity distribution of lights emitted from light-emitting particles in the light detection region and detected exists. Thus, the light intensity range for the signal to be extracted as a signal of a light-emitting particle on the time series light intensity data may be set based on the shape of the distribution of the intensities of the signals against function values of positions in the light detection region determined based on the signal generation frequency integrated value distribution, or based on the shape of the signal generation frequency integrated value distribution itself. Also, the region where the deviation in the distribution of the intensities of the signals against function values of positions in the light detection region determined based on the signal generation frequency integrated value distribution from the bell shaped profile of the intensity distribution of the lights emitted from the light-emitting particle in the light detection region and detected exists can be judged from the slope of the intensities of signals to function values of positions in the distribution of the intensity of the signals against function values of positions in the light detection region determined based on the signal generation frequency integrated value distribution. Thus, the light intensity range for the signal to be extracted as a signal of a light-emitting particle on the time series light intensity data may be set based upon the slope of the intensities of signals to function values of positions in the distribution of the intensity of the signals against function values of positions in the light detection region determined based on the signal generation frequency integrated value distribution.

Furthermore, in the above-mentioned inventive device, in order to enable a user of the device to easily grasp the signal generation frequency integrated value distribution and/or the distribution of the intensities of signals against function values of positions in the light detection region determined based on the signal generation frequency integrated value distribution, the signal processor may have a display which can display the distribution of the intensities of the signals against function values of positions in the light detection region determined based on the signal generation frequency integrated value distribution and/or the signal generation frequency integrated value distribution. And, it may be designed that, on the distribution of the intensities of the signals against function values of positions in the light detection region or the signal generation frequency integrated value distribution displayed in the display, the user of the device can set the light intensity range for the signal to be extracted as a signal of a light-emitting particle on the time series light intensity data. According to this structure, the user of the device can set the intensity range to be set as the light intensity range for the signal to be extracted as a signal of a light-emitting particle on the time series light intensity data while visually checking it, and thus, the operation for setting the light intensity range becomes advantageously easier.

In one of manners of the above-mentioned present invention, the number of light-emitting particles encompassed in the light detection region may be counted by counting the number of the selectively detected signals (The counting of particles.). In that case, by associating the number of the detected light-emitting particles with the moving amount of the position of the light detection region, the information on the number density or concentration of the light-emitting particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the light-emitting particle can be concretely computed.

With respect to the moving of the position of the light detection region in the above-mentioned inventive structure, the moving speed of the position of the light detection region in the sample solution may be appropriately changed based on the characteristic or the number density or concentration of the light-emitting particle in the sample solution. As understood in a person skilled in the art, the condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Furthermore, with respect to the above-mentioned moving of the position of the light detection region, the moving speed of the position of the light detection region in the sample solution is preferably set to be higher than the diffusional moving velocity of a light-emitting particle (the average moving speed of a particle owing to the Brownian motion). As explained above, in the present invention, a light-emitting particle will be detected individually by detecting the light emitted from a light-emitting particle in the light detection region. However, when the light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of a light-emitting particle thereby it becomes possible to make one light-emitting particle correspond to one signal. In this regard, since the diffusional moving velocities differ depending upon light-emitting particles, it is preferable that the moving speed of the light detection region can be changed appropriately according to the characteristics (especially, the diffusion constant) of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement, track of the position of the light detection region may be set arbitrarily, for example, which is selectable from circular, elliptical, rectangular, straight and curvilinear ones. In this connection, in the present invention, since the position of the light detection region is moved by changing the optical path of the optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow.). Further, since no structure for flowing to sample solution is required, the measurement and analysis can be conducted with a small amount of the sample solution (at the level of one to several tens of μL) similarly to FCS, FIDA, etc.

The processes of the unique optical analysis technique of conducting a light detection with moving the position of a light detection region in a sample solution and detecting the signal from each light-emitting particle individually in the above-mentioned inventive device can be realized with a general-purpose computer. Thus, according to another aspect of the present invention, there is provided a computer readable storage device having a computer program product including programmed instructions for optical analysis for detecting light from a light-emitting particle dispersed and moving at random in a sample solution using an optical system of a confocal microscope or a multiphoton microscope, said programmed instructions causing a computer to perform steps of moving a position of a light detection region of the optical system of the microscope in the sample solution by changing an optical path of the optical system; detecting light from the light detection region during moving the position of the light detection region in the sample solution and generating time series light intensity data, and detecting a signal from each light-emitting particle individually in the time series light intensity data, wherein the signal from each light-emitting particle is detected by extracting, as the signal of the light-emitting particle from a group of signals detected in the time series light intensity data, a signal having a light intensity in a light intensity range having been set based upon a signal generation frequency integrated value distribution which is a distribution, obtained by using as a variable an intensity of a signal detected in the time series light intensity data, of integrated values of generation frequencies of signals having an intensity not lower than the variable. In the present application, "computer readable storage device" does not cover transitory propagating signal per se. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, semiconductor memory, etc. Furthermore, the above-mentioned program may be distributed to a computer through communication line, and the computer which received this distribution may be made to execute the program.

Also in this computer program, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles. Further, in the step of moving the position of a light detection region, the position of the light detection region may be moved at a predetermined velocity or at a velocity quicker than the diffusion moving velocity of a light-emitting particle, and the moving speed of the position of the light detection region may be set based on a characteristics of a light-emitting particle or its number density or concentration in the sample solution. The movement track of the position of the light detection region may be selectable from a circle, an ellipse, a rectangle, a straight line and a curve line. And, in the above-mentioned computer program, the light intensity range set based on the signal generation frequency integrated value distribution may be a light intensity range in which the intensity distribution of the signals against positions in the light detection region determined based on the signal generation frequency integrated value distribution substantially accords with the intensity distribution of lights emitted from the light-emitting particles in the light detection region and detected, and preferably, in the step of detecting the signal from each light-emitting particle individually, a signal having an intensity beyond a threshold value determined based on the signal generation frequency integrated value distribution on the time series light intensity data may be extracted as a signal of a light-emitting particle, or in the step of detecting the signal from each light-emitting particle individually, the upper limit of noise intensities in time series light intensity data may be determined based on the signal generation frequency integrated value distribution.

Moreover, in the above-mentioned computer program, the light intensity range for the signal to be extracted as a signal of a light-emitting particle on the time series light intensity data may be set based on a fitting error when the fitting of a bell type function is carried out to the distribution of the intensity of the signals against function values of positions in the light detection region determined based on the signal generation frequency integrated value distribution, based on the shape of the distribution of the intensities of the signals against function values of positions in the light detection region determined based on the signal generation frequency integrated value distribution, based on the shape of the signal generation frequency integrated value distribution, or based on the slope of the intensities of the above-mentioned signals to function values of positions in the distribution of the intensities of the signals against function values of positions in the light detection region determined based on the signal generation frequency integrated value distribution. Furthermore, the above-mentioned computer program may comprise a step of displaying on a display the distribution of the intensities of signals against function values of positions in the light detection region determined based on the signal generation frequency integrated value distribution and/or the signal generation frequency integrated value distribution, and in the step of detecting the signal from each light-emitting particle individually, the light intensity range for the signal to be extracted as a signal of a light-emitting particle on the time series light intensity data may be settable on the distribution of the intensities of the signals against function values of positions in the light detection region or the signal generation frequency integrated value distribution displayed on the display.

Furthermore, according to the above-mentioned inventive device or computer program, there is realized a novel optical analysis method of detecting light of each light-emitting particle with moving the position of a light detection region in a sample solution, wherein the detection of a signal of a light-emitting particle is performed with reference to the signal generation frequency integrated value distribution. Accordingly, according to the present invention, there is provided an optical analysis method of detecting light from a light-emitting particle dispersed and moving at random in a sample solution using an optical system of a confocal microscope or a multiphoton microscope, characterized by comprising steps of: moving a position of a light detection region of the optical system of the microscope in the sample solution by changing an optical path of the optical system; detecting intensity of light from the light detection region during moving the position of the light detection region in the sample solution and generating time series light intensity data, and detecting a signal indicating light from the light-emitting particle individually on the time series light intensity data, wherein, in the step of detecting a signal indicating light from the light-emitting particle individually, the signal from each light-emitting particle is detected by extracting, as the signal of the light-emitting particle from a group of signals detected in the time series light intensity data, a signal having a light intensity in a light intensity range having been set based upon a signal generation frequency integrated value distribution which is a distribution, obtained by using as a variable an intensity of a signal detected in the time series light intensity data, of integrated values of generation frequencies of signals having an intensity not lower than the variable.

Also in this method, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles. Furthermore, in the step of changing the optical path of an optical system to move the position of the light detection region, the position of the light detection region may be moved at a predetermined velocity or at a velocity quicker than the diffusion moving velocity of a light-emitting particle, and the moving speed of the position of the light detection region may be set based on a characteristics of a light-emitting particle or its number density or concentration in the sample solution. The movement track of the position of the light detection region may be selectable from a circle, an ellipse, a rectangle, a straight line and a curve line. And in the above-mentioned method, the light intensity range set based on the signal generation frequency integrated value distribution may be a light intensity range in which the intensity distribution of the signals against positions in the light detection region determined based on the signal generation frequency integrated value distribution substantially accords with the intensity distribution of lights emitted from the light-emitting particles in the light detection region and detected, and preferably, in the step of detecting the signal from each light-emitting particle individually, a signal having an intensity beyond a threshold value determined based on the signal generation frequency integrated value distribution on the time series light intensity data may be extracted as a signal of a light-emitting particle, or in the step of detecting the signal from each light-emitting particle individually, the upper limit of noise intensities in time series light intensity data may be determined based on the signal generation frequency integrated value distribution.

Also in the above-mentioned method, the light intensity range for the signal to be extracted as a signal of a light-emitting particle on the time series light intensity data may be set based on a fitting error when the fitting of a bell type function is carried out to the distribution of the intensity of the signals against function values of positions in the light detection region determined based on the signal generation frequency integrated value distribution, based on the shape of the distribution of the intensities of the signals against function values of positions in the light detection region determined based on the signal generation frequency integrated value distribution, based on the shape of the signal generation frequency integrated value distribution, or based on the slope of the intensities of the above-mentioned signals to function values of positions in the distribution of the intensities of the signals against function values of positions in the light detection region determined based on the signal generation frequency integrated value distribution. Furthermore, in the case that the distribution of the intensities of signals against function values of positions in the light detection region determined based on the signal generation frequency integrated value distribution and/or the signal generation frequency integrated value distribution is/are displayed on an arbitrary display device, in the step of detecting a signal from a light-emitting particle individually, the light intensity range for the signal to be extracted as a signal of a light-emitting particle on the time series light intensity data may be settable on the distribution of the intensities of the signals against function values of positions in the light detection region or the signal generation frequency integrated value distribution displayed on the display device.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Generally, in the inventive optical analysis technique, using the knowledge that the intensity range of noises can be easily determined by referring to the generation frequency distribution of signals on time series light intensity data (the signal generation frequency integrated value distribution) in the scanning molecule counting method, the labor and time taken for the extraction of a signal of a light-emitting particle from time series light intensity data will be reduced substantially. Especially, in principal, the light intensity range for the signal to be extracted as a signal of a light-emitting particle defined based on the signal generation frequency integrated value distribution does not vary for light-emitting particles having the same brightness (light-emitting particles whose emitting light intensities are substantially equal to one another under a certain same emission condition), and therefore, in measurements by the scanning molecule counting method for various sample solutions with light-emitting particles having the equivalent brightness, the above-mentioned light intensity range determined for one certain sample solution can be used also for the measurements of the other sample solutions unless the measurement conditions, such as setups of the device, change, and thereby it becomes possible to reduce the trial and error for determining the criterion for detection of a signal of a light-emitting particle with eliminating noise signals. And, since noise exclusion becomes quicker, the range of sample solutions which can be used in the scanning molecule counting method is expanded and it is expected that the application range of the scanning molecule counting method, such as an observation of intermolecular interaction and analysis, will be expanded.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the inventive optical analysis technique is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution.

FIGS. 2A and 2B are a schematic diagram explaining the principle of the light detection and a schematic diagram of the variation of the measured light intensity with time in the scanning molecule counting method to which the inventive optical analysis technique is applied, respectively. FIG. 2C is a schematic diagram of the cross sectional view of the light detection region seen from the light travelling direction of the microscope, and FIG. 2D is a schematic diagram of an example of a time series light intensity data measured in FIG. 2C. FIG. 2E is a diagram showing an intensity distribution of signals of light-emitting particles against radial direction positions r from the maximum intensity point Imax of the light detection region (thick solid line). On this, an intensity distribution (thin solid line) of actual signals in a case of noise signals (dotted line) are present is shown schematically.

FIGS. 3A and 3B are diagrams showing the procedures of the scanning molecule counting method performed in accordance with the present invention in the form of a flow chart.

FIGS. 4A and 4B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 4C shows drawings explaining an example of the signal processing step of the detected signals in the procedure for detecting the existence of a light-emitting particle from the measured time series light intensity data (change in time of photon count) in accordance with the scanning molecule counting method.

Figure 5:
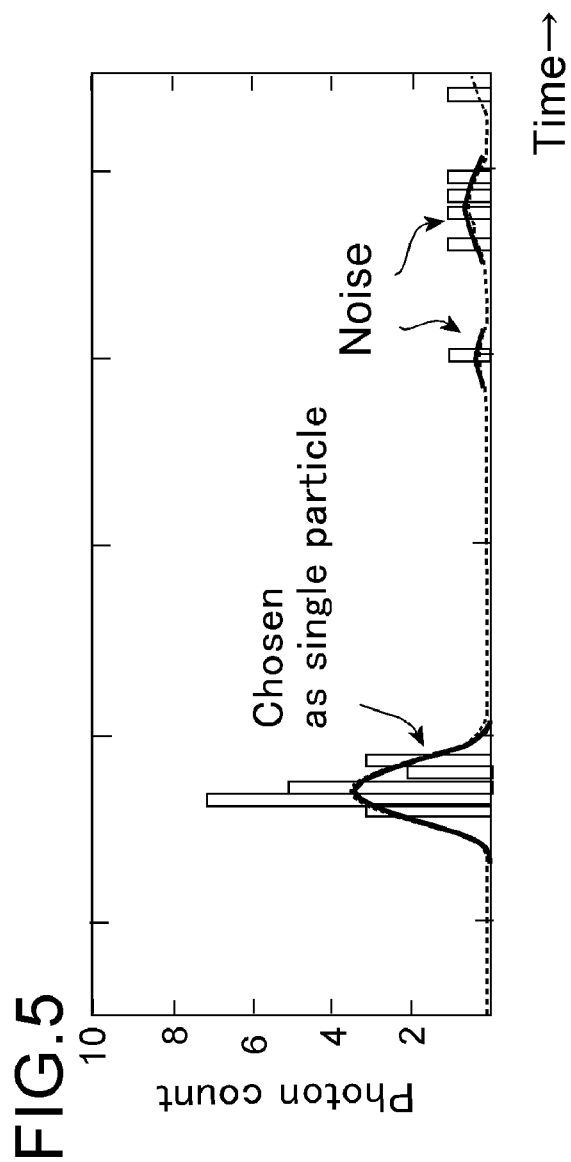

FIG. 5 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or a contaminant.

Figure 6A:
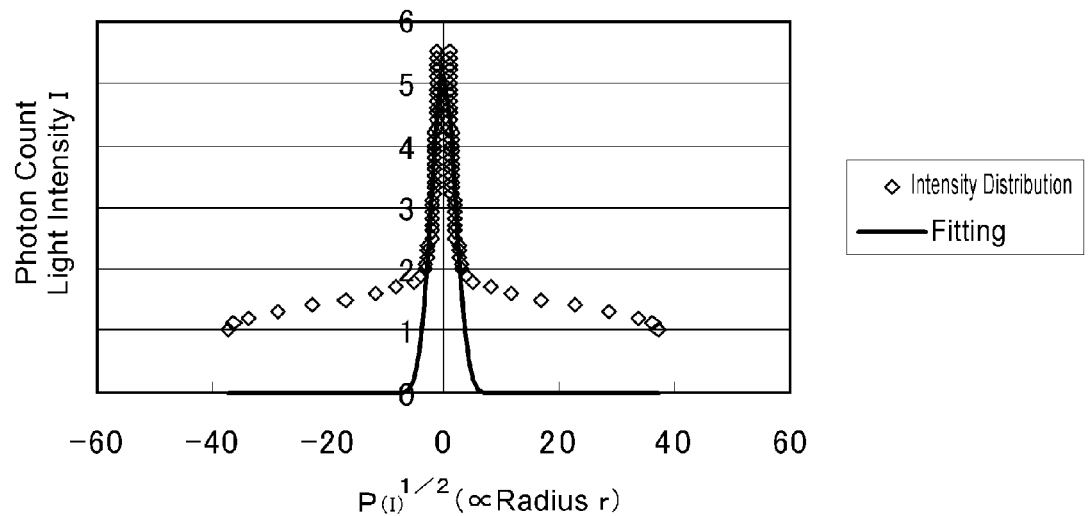
Figure 6B:
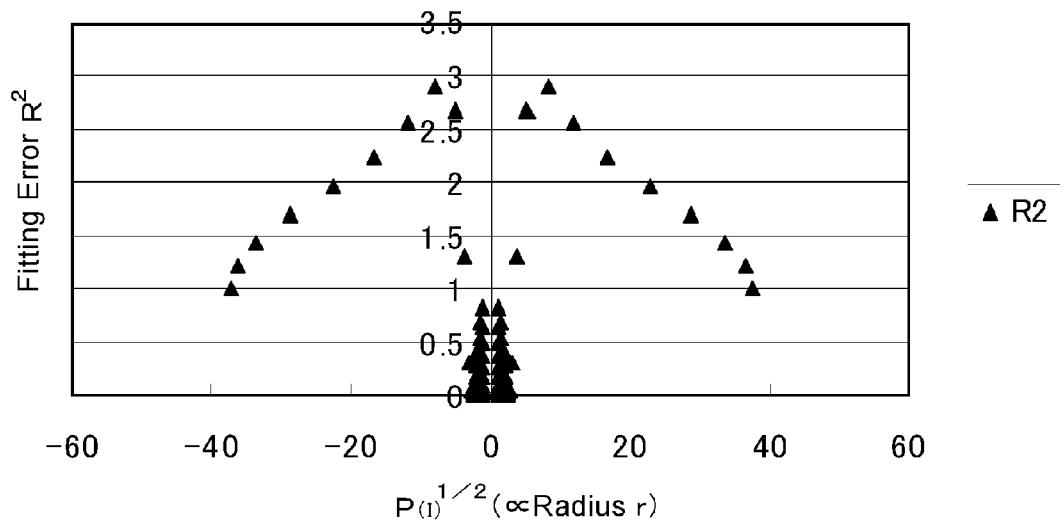

FIG. 6A is a diagram in which the light intensities I are plotted against square roots $P^{1/2}$ of the number P(I) of signals having an intensity more than the light intensity (photon count) I in time series light intensity data. In the diagram, the fitting curve to plots is also drawn. FIG. 6B is a diagram in which errors $R^2$ of plots of the light intensities I against square roots $P^{1/2}$ of the numbers P(I) of signals having an intensity more than the light intensity (photon count) I in FIG. 6A from the fitting curve are plotted against square roots $P^{1/2}$ of the numbers P(I) of signals.

Figure 7A:
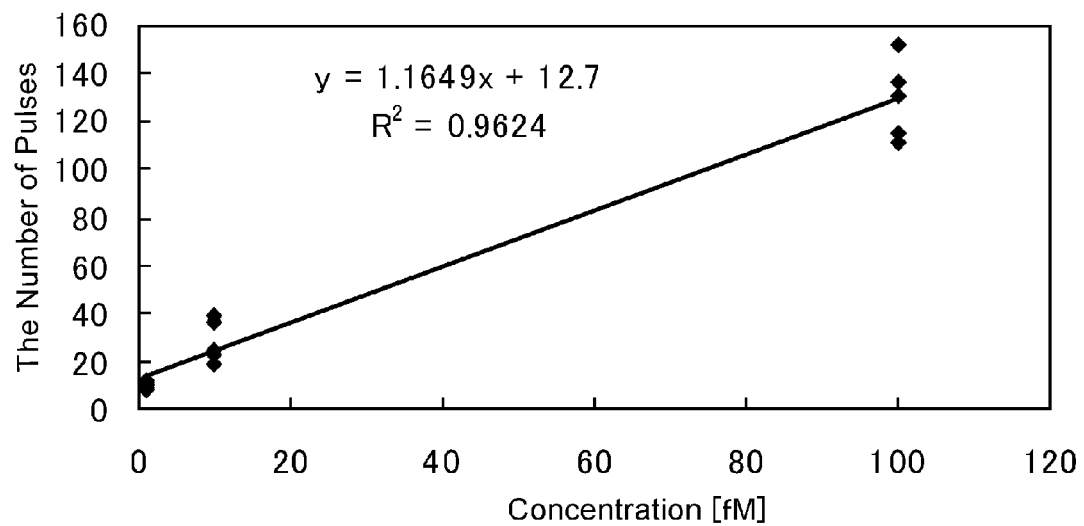
Figure 7B:
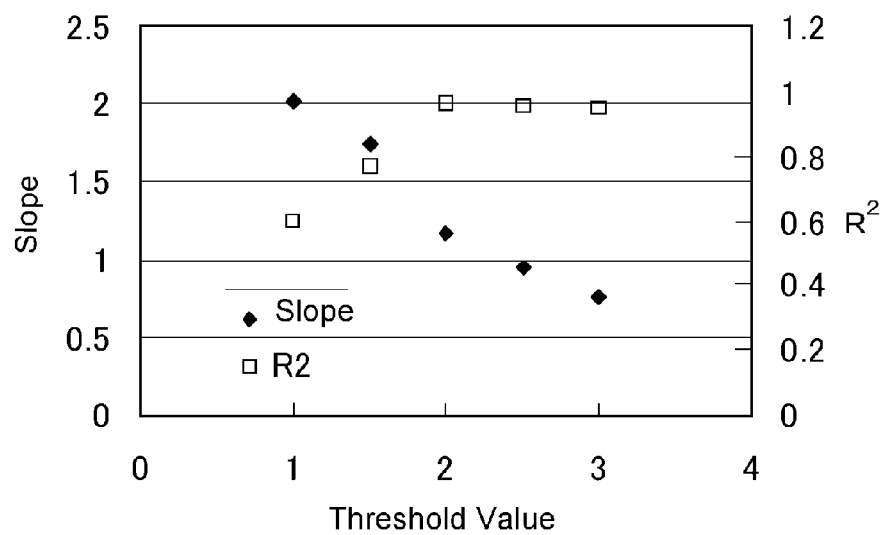

FIG. 7A is a graph of the numbers of pulses detected as signals of light-emitting particles measured by the scanning molecule counting method (embodiment 1) performed for sample solutions containing the light-emitting particles at various concentrations according to the inventive optical analysis technique. The threshold value for extraction of the signals of light-emitting particles was set to 2 based on the signal generation frequency integrated value distribution. The solid line in the drawing shows the approximate straight line of the numbers of pulses against light-emitting particle concentrations by the least-squares method. FIG. 7B is a drawing in which the slopes (♦) and correlation coefficients (□) of the approximate lines for the numbers of pulses against light-emitting particle concentrations when the threshold value was set to 1 to 3 are plotted against set threshold values.

FIG. 8 show examples of the time variation of the photon count (light intensity) obtained in a conventional optical analysis technique computing fluorescence intensity fluctuation, where FIG. 8A shows a case that the particle concentration is at a level providing a sufficient precision in the measurement, and FIG. 8B shows a case that the particle concentration in a sample is significantly lower than the case of FIG. 8A.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

Structure of Optical Analysis Device

In the basic structure, the optical analysis technique according to the present invention can be realized with an optical analysis device constructed by associating the optical system of a confocal microscope and a photodetector, enabling FCS, FIDA, etc., as schematically illustrated in FIG. 1A. Referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL in this optical analysis device, which is called as "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity is reduced to $1/e^2$ of the peak intensity. Then, the light having passed through the pinhole 13 passes through the dichroic mirror 14a and transmits through the corresponding barrier filter 14 (where a light component only in a specific wavelength band is selected); and is introduced into a mutt mode fiber 15, reaching to the corresponding photodetector 16, and after the conversion into time series electric signals, the signals are inputted into the computer 18, where the processes for optical analyses are executed in manners explained later. For the photodetector 16, preferably, a super high sensitive photodetector, usable for the photon counting, is used, so that the light from a single light-emitting particle, for example, the faint light from one or several fluorescent dye molecule(s), can be detected. When the detection of light is performed by the photon counting, the measurement of light intensity is performed for a predetermined time in a manner of measuring the number of photons which have sequentially arrived at a photodetector in every predetermined unit time (BIN TIME). Thus, in this case, the time series light intensity data is time series photon count data.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetector 16 under the control of the computer 18. The movement, track of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. When a light-emitting particle emits light owing to phosphorescence or scattered light, the above-mentioned optical system of the confocal microscope is used as it is. Further, in the case that a light-emitting particle emits light owing to a chemiluminescence or bioluminescence phenomenon without excitation light, the optical system 2-5 for generating excitation light may be omitted. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may also be provided so as to detect the lights from light-emitting particles of two or more kinds having different light-emitting wavelengths, if contained in a sample, separately, depending upon the wavelengths. The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

The Principle of the Inventive Method

As described in the column of "Summary of Invention", briefly, in the inventive optical analysis technique, it is tried to determine easily the criterion for eliminating noises and detecting a signal of a light-emitting particle with reference to a distribution of generation frequencies of the light intensities in time series light intensity data (signal generation frequency integrated value distribution) in the scanning molecule counting method. In the following, the principles of the scanning molecule counting method and noise exclusion of the present invention are explained.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques, such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 8A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn on FIG. 8B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring time should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

As the processes to be performed in the scanning molecule counting method, briefly speaking, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2A. Then, for example, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

2. Determination of Light Intensity Range for Extraction of a Signal of a Light-Emitting Particle Using Signal Generation Frequency Integrated Value Distribution As already noted, on the data of light intensity temporally acquired with the photodetector 16 by the above-mentioned scanning molecule counting method (time series light intensity data), there exist noises due to heat noises of a photodetector, a background light, etc. other than signals of light-emitting particles. Thus, in the detection of a signal of a light-emitting particle, the process for extraction of the signal of the light-emitting particle from time series light intensity data is needed. For the process of extracting a signal of a light-emitting particle, typically, with reference to the intensity of a signal on time series light intensity data, there is conducted a process of extracting as a signal of a light-emitting particle a signal having an intensity within a predetermined intensity range, more concretely, a signal having an intensity not less than or beyond a predetermined threshold value. However, so far, an explicit criterion for extracting a signal of a light-emitting particle and excluding noises is not found out, and therefore, the above-mentioned predetermined intensity range or threshold value is defined by trial and error or experience of a user of the device, and this fact requires the labor and time for the detection of a signal of a light-emitting particle and could cause the deterioration of the accuracy of the detected result of the signal of the light-emitting particle.

In this connection, as already noted, the inventor of the present invention has found that, with reference to the signal generation frequency integrated value distribution on time series light intensity data, the intensity range of signals of light-emitting particles and the intensity range of noises can be estimated, respectively, and the above-mentioned predetermined light intensity range or threshold value for extraction of a signal of a light-emitting particle can be easily determined based on the signal generation frequency integrated value distribution. In the following, the principle of the determination of the light intensity range for extraction of a signal of a light-emitting particle using the signal generation frequency integrated value distribution of time series light intensity data is explained.

Referring to FIGS. 2C-2E, in the light detection region CV, the intensity of light which is emitted from the light-emitting particle passing therethrough and reaches to a photodetector varies depending upon the position of the light-emitting particle in the light detection region CV, and thus, the detected light intensities of light-emitting particles, even having the same brightness (light-emitting particles whose emitting light intensity are substantially equal to one another in the observation under the same condition), differs depending upon the passing positions of the light-emitting particles in the light detection region. For instance, in a case that a certain light-emitting particle is a particle emitting light, with the irradiation with illumination light, typically, the light intensity of the illumination light in the light detection region is maximized in the almost center of the light detection region (light condensing region) and decreases from this maximum intensity point in the almost radial direction. Accordingly, the light intensity from a light-emitting particle becomes its maximum when it crosses the almost center of the light detection region, and as the position of the light-emitting particle approaches the circumference of the light detection region, its light intensity is gradually reduced. Namely, when the position in the light detection region is represented with the distance in the radial direction (radius r) from the maximum intensity point, the distribution of the intensity of light emitted from a light-emitting particle in the light detection region and detected is a bell shaped distribution against radii r from the maximum intensity point as illustrated with the thick solid line in FIG. 2E. For example, even when light-emitting particles α, β and γ in FIG. 2C are particles having the same brightness, the detected light intensities are mutually different depending upon the routes through which the respective light-emitting particles have passed, so that in the drawing, the light intensity of the light-emitting particle β passing the almost center of the light detection region becomes higher than the light intensities of the light-emitting particles α and γ (see FIG. 2D).

When the distribution of the light intensities, emitted from light-emitting particles in the light detection region and detected, has a profile like the thick solid line in FIG. 2E, since it is considered that the light-emitting particles are distributed almost uniformly in a sample solution, so that the number of light-emitting particles passing the light detection region increases as the distance in the radial direction from the maximum intensity point becomes longer, and therefore the frequency distribution against intensities of signals of light-emitting particles encompassed in the light detection region and detected during the moving of the light detection region becomes a distribution having a smaller frequency (the axis of abscissa of FIG. 2E) as the light intensity (the axis of ordinate of FIG. 2E) becomes larger in accordance with the distribution of the light intensities emitted from light-emitting particles in the light detection region and detected as the thick solid line in FIG. 2E.

More concretely, first, a distribution of the intensities of lights emitted from light-emitting particles in the light detection region and detected as illustrated with the thick solid line in FIG. 2E can be approximated with a Lorentz function, the light intensity I at the radius r from the maximum intensity point Imax of the distribution can be given by:

[Exp. 1]

$$I = \frac{w^2 I_{max}}{r^2 + w^2} + I_{bg}, \quad (1)$$

using the maximum Imax of the light intensity distribution (Imax is equivalent to the maximum light intensity of a single light-emitting particle.), the half width w at the half maximum of distribution and the intensity background Ibg. On the other hand, when the light detection region is moved at the scanning speed u during the time t in a sample solution of a concentration c of a certain light-emitting particle, supposing the cross sectional area of a small region which gives a light intensity more than the light intensity I in the direction vertical to the moving direction in the light detection region is S, the total number P of the signals of the light-emitting particles having the intensity more than the light intensity I is:

$$P = cSutN_A \quad (2)$$

($N_A$ is the Avogadro's number). Here, supposing the cross sectional area S of the small region which gives the light intensity more than the light intensity I is approximately given by $S = \pi r^2$ (more strictly, although the cross section of the light detection region is elliptical, it is approximated with a circle for simplifying calculations. The same in the followings.), the radius r is represented by

[Exp. 2]

$$r = \sqrt{\frac{P}{cN_A ut\pi}}, \quad (3)$$

and thus, consequently, the square root of the number P of the signals of the light-emitting particles having the light intensity more than the light intensity I will be proportional to the radius of the cross sectional area of the small region which gives the light intensity I (It can be said that the square root of the number P of the signals is function values of radii r expressing positions in the light detection region.). Then, the distribution of the numbers P(I) of the signals of the light-emitting particles having the light intensity more than the light intensity I, the signal generation frequency integrated value distribution can be given from Expressions (1) and (2) by:

[Exp. 3]

$$P(I) = cutN_A \pi w^2 \left( \frac{I_{max}}{I - I_{bg}} - 1 \right) \quad (4)$$

Further, from the relation of Expressions (1) and (3), the distribution of the light intensities I as in FIG. 2E can be approximated with a Lorentz function using as its variable the square root of the number P of the signals of light-emitting particles as follows:

[Exp. 4]

$$I = \frac{w^2 I_{max}}{\frac{(\sqrt{P})^2}{cN_A ut\pi} + w^2} + I_{bg} \quad (5)$$

Thus, for signals of light-emitting particles on time series light intensity data, with reference to the distribution of the light intensities I against square roots of the numbers of signals P of the light-emitting particles having the light intensity more than the light intensity I, the distribution of the intensities of lights emitted from the light-emitting particles in the light detection region and detected can be estimated. For example, after obtaining the number of signals P of light-emitting particles having the light intensity more than the light intensity I in every light intensity I the preparation of the signal generation frequency integrated value distribution), by plotting the light intensities I against radii r computed from square roots of the numbers of signals P of light-emitting particles and further drawing the plots of the light, intensities I symmetrically with respect to the axis of the square root of the number of signals P=0, the profile of the distribution of the intensities of lights emitted from light-emitting particles in the light detection region and detected can be drawn as the thick solid line in FIG. 2E.

Furthermore, when the distribution of the intensities of lights emitted from light-emitting particles in the light detection region and detected can be approximated by a Gauss function, the light intensity I at the distance r from the maximum intensity point Imax of the distribution is:

[Exp. 5]

$$I = I_{max} \exp\left(-\frac{r^2}{2\pi w^2}\right) + I_{bg}, \quad (6)$$

and thus, the signal generation frequency integrated value distribution can be expressed by:

[Exp. 6]

$$P(I) = 2w^2 \ln\left(\frac{I_{max}}{I - I_{bg}}\right) \cdot cutN_A \quad (7)$$

And, the distribution of the light intensities I as in FIG. 2E can be approximated by the Gauss function using as its variable the square root of the number of signals P of light-emitting particles as follows:

[Exp. 7]

$$I = I_{max} \exp\left(-\frac{(\sqrt{P})^2}{2\pi^2 w^2 cN_A ut}\right) + I_{bg} \quad (8)$$

On the other hand, with respect to noise signals, the distribution of their intensities is not dependent on the distribution of the intensities of lights emitted from light-emitting particles in the light detection region and detected, and thus, the distribution of the noise intensities against the square root of the number of signals (the signal generation frequency integrated value distribution) has a profile as the dotted line in FIG. 2E. Then, the distribution (the signal generation frequency integrated value distribution) of the intensities against the square root of the numbers of signals for all the signals in time series light intensity data has the profile as drawn in the thin solid line obtained by the composition of the distribution for the signals of light-emitting particles drawn in the thick solid line and the distribution for noise signals drawn in the dotted line in FIG. 2E. In the profile of this thin solid line, as understood from the drawing, the profile discontinuously bends on the maximum of the distribution for the noise signals and expands in the lateral direction, and accordingly, its shape deviates from the bell type function of the distribution of the intensities of lights emitted from the light-emitting particles in the light detection region and detected. Therefore, it will be understood that the signals having the intensity more than the light intensity at the maximum of the distribution of the noise signals, i.e., the discontinuity of the profile, is a signal of a light-emitting particle, and the noise signals are included in the signals below the maximum of the distribution of the noise signals. Thus, by detecting or specifying the discontinuity of the profile of the intensity distribution against the square root of the numbers of signals for all the signals in time series light intensity data; defining the light intensity range more than the light intensity of the discontinuity as the light intensity range for extraction of the signal of a light-emitting particle, namely, determining the intensity of the discontinuity of the profile as the threshold value Ith; and extracting the signal(s) of more than the threshold value Ith, the detection of the signal of a light-emitting particle becomes possible with the influences of noise signals having been eliminated substantially. In this regard, the extracting of only the signals of more than the threshold value Ith as signals of light-emitting particles corresponds to detecting only the light-emitting particle which passes through the inside of a small region of the radius r from the maximum intensity point in the light detection region, namely, namely, reducing the region in which a light-emitting particle is detected.

Operation Processes of Scanning Molecule Counting Method

In the embodiment of the scanning molecule counting method in accordance with the present invention with the optical analysis device 1 as illustrated in FIG. 1A, concretely, there are conducted (1) preparation of a sample solution containing light-emitting particles; (2) process of measuring the light intensity of the sample solution and (3) process of analyzing measured light intensities. FIGS. 3A and 3B shows the processes in this embodiment in form of the flow chart.

(1) Preparation of a Sample Solution

The particle to be observed in the inventive method may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particle (Typically, the sample solution is an aqueous solution, but not limited to this, and it may be an organic solvent, or other arbitrary liquids.). Also, the particle to be observed may be a particle which emits light by itself, or may be a particle to which a light emitting label to fluorescence molecule, a phosphorescence molecule, and a chemiluminescent or bioluminescent molecule) is attached in an arbitrary manner.

(2) Measurement of the Light Intensity of a Sample Solution

In the process of measuring the light intensity in the optical analysis by the scanning molecule counting method of the present embodiment, the measurement of light intensity is performed with driving the mirror deflector 17 to move the position of the light detection region in a sample solution (scanning in a sample solution) (FIG. 3A—step 100). In the operation processes, typically, after dispensing a sample solution into the well(s) 10 of the micro plate 9 and putting it on the stage of the microscope, when a user inputs to the computer 18 a command of staring a measurement, the computer 18 executes programs memorized in a storage device (not shown) (the process of changing the optical path in order to move the position of the light detection region in the sample solution, and the process of detecting light from the light detection region during the moving of the position of the light detection region) to start radiating the excitation light and measuring the light intensity in the light detection region. When the measurement was started, under the control of the operation process of the computer 18 according to the programs, from the light source 2, the light of the excitation wavelength of a light-emitting particle in the sample solution is emitted, and the mirror deflector 17 drives the mirror 7 (galvanomirror) to move the position of the light detection region in the well 10, and simultaneously with this, the photodetector 16 sequentially converts the detected light into an electric signal and transmits it to the computer 18, which generates the time series light intensity data from the transmitted signals and stores it in an arbitrary manner. The photodetector 16 is typically a super high sensitive photodetector which can detect an arrival of a single photon, and thus the detection of light may be the photon counting performed for a predetermined time in the manner of measuring sequentially the number of photons which arrive at the photodetector for every predetermined unit time (BIN TIME), for example, every 10 μs, and accordingly the time series light intensity data will be a time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected light emitting particles, the region size or volume through which the light detection region has passed is required, and therefore, preferably, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

By the way, regarding the moving speed of the position of the light detection region, in order to perform quantitatively precisely individual detection of a light-emitting particle to be observed from the measured time series light intensity data or the counting of the number of light-emitting particles, it is preferable that the moving speed is set to a value quicker than the moving speed in the random motion, i.e., Brownian motion of a light-emitting particle. Since the light-emitting particle to be the observation object in this embodiment is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 4A, whereby the light intensity changes at random (the excitation light intensity in the light detection region is reduced from the peak at the center of the region toward its outside.), so that it becomes difficult to determine a significant light intensity change corresponding to each light-emitting particle (a signal indicating light from a light-emitting particle). Then, preferably, as drawn in FIG. 4B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost uniform in the time series light intensity data as illustrated in the upper row of FIG. 4C (When a light-emitting particle passes through the light detection region in an approximately straight line, the profile of the light intensity change is similar to the excitation light intensity distribution.) and the correspondence between each light-emitting particle and light intensity can be easily determined.

Concretely, the time $\Delta t$ required for a light-emitting particle having a diffusion coefficient D to pass through the light detection region of radius Wo (confocal volume) by the Brownian motion is given from Expression of the relation of mean-square displacement:

$$(2Wo)^2 = 6D \cdot \Delta t \tag{9}$$

as:

$$\Delta t = (2Wo)^2/6D \tag{10},$$

and thus, the velocity of the light-emitting particle moving by the Brownian motion (diffusional moving velocity) Vdif, becomes approximately $$V\text{dif} = 2Wo/\Delta t = 3D/Wo \tag{11}$$

Then, with reference to this, the moving speed of the position of the light detection region may be set: to a value sufficiently quicker than Vdif. For example, when the diffusion coefficient of a light-emitting particle is expected to be about $D=2.0\times10^{-10}$ m$^2$/s, Vdif will be $1.0\times10^{-3}$ m/s, supposing Wo is about: 0.62 μm, and therefore, the moving speed of the position of the light detection region may be set to its 10 times or more, 15 mm/s. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data in the sample solution is obtained by the above-mentioned processes, there are performed detection of signals on the light intensity data, determination of a threshold value for extraction of a signal of a light-emitting particle, extraction of a signal of a light-emitting particle, counting of light-emitting particles, and various analyses, such as concentration calculation, etc. in the computer 18 through processes in accordance with programs memorized in a storage device.

(i) Detection of a Signal on Time Series Light Intensity Data

As already noted, when the track of one light-emitting particle in its passing through the light detection region is approximately straight as shown in FIG. 4B, the light intensity variation in the signal corresponding to the particle in the time series light intensity data has a bell shaped profile reflecting the light intensity distribution in the light detection region (determined by the optical system). Thus, basically in the scanning molecule counting method, when the time width $\Delta \tau$ for which the light intensity value exceeding an appropriately set threshold value Ith continues is in a predetermined range, the signal having the profile of the light intensity may be judged to correspond to one particle having passed through the light detection region, and thereby one light-emitting particle is detected. And a signal whose light intensity does not exceed the threshold value Ith or which does not have time width $\Delta \tau$ in the predetermined range is judged as noise or a signal of a contaminant. Further, when the light intensity distribution in the light detection region can be assumed as Gaussian distribution:

$$I = A \cdot \exp(-2t^2/a^2) \tag{12},$$

and when the intensity A and the width a, computed by fitting Expression (12) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

However, as already noted, in the first place, in order to determine the threshold value Ith for removing noise signals from the signals found out in time series light intensity data, it is necessary to grasp the intensities of the noise signals. Then, in the inventive optical analysis technique, first, as described in the explanations in conjunction with FIGS. 2C-2E, the signal generation frequency integrated value distribution is prepared from the signals of time series light intensity data, and based on this distribution, the threshold value Ith is determined. After this, a signal which has an intensity more than the threshold value Ith among the signals found out in time series light intensity data is extracted as a signal of a light-emitting particle.

As an example of the process of the detection of signals in time series light intensity, first, a smoothing treatment is performed to the time series light signal data (FIG. 4C, the most upper row "detected result (unprocessed)") (FIG. 3A—step 110, FIG. 4C mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 4C, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data (Steps 130-160). Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 4C, the lower row "bell-shaped function fitting"), and then, parameters of the pulse of the bell-shaped function, such as the peak intensity (the maximum), Ipeak; the pulse width (full width at half maximum). Wpeak; the correlation coefficient in the fitting (of the least square method), etc. are computed (step 140). In this regard, although the bell-shaped function to be used in the fitting is typically Gauss function as in Expression (8), it may be Lorentz type function.

And, it is judged whether or not computed parameters of the pulse, such as the peak intensity, pulse width and correlation coefficient, are in the corresponding predetermined ranges, respectively, and the signal whose each parameter of the bell shaped function is in the corresponding predetermined range is detected (step 150). Here, basically, the predetermined ranges for the peak intensity, pulse width, and correlation coefficient of a pulse are set as the ranges assumed for the parameters of a bell shaped profile drawn by a pulse signal detected when one light-emitting particle passes through the light detection region, and thereby, the signal assumed to be a signal of a light-emitting particle will be detected from the time series light intensity data. However, as already noted, no clear criterion for eliminating noise signals has been known at this stage. Thus, in this step, a provisional value which may be set appropriately is used as the threshold value for the peak intensity of a pulse (The provisional value may be any value expected to be lower than the maximum of the noise signal intensities.), and signals of more than this threshold value are extracted. Accordingly, the signal, whose computed parameters of the bell-shaped function are judged to be within the ranges provisionally set as assumed in a light signal corresponding to one light-emitting particle, as shown in FIG. 5 left, is provisionally judged as a signal corresponding to one light-emitting particle. On the other hand, a pulse signal, whose computed parameters of the bell-shaped function are not within the assumed ranges, as shown in FIG. 5 right, is disregarded as noise.

The searching and judging of a pulse signal in the above-mentioned processes of steps 130-150 are repetitively carried out throughout time series light intensity data (step 160). In this connection, the processes for detecting individually a signal provisionally judged as a signal of a light-emitting particle from the time series light intensity data may be performed by an arbitrary way, other than the above-mentioned procedures.

(ii) Determination of a Threshold Value

When pulse signals have been detected on the time series light intensity data through the processes of the above-mentioned steps 130-160, the true threshold value for extraction of a signal of a light-emitting particle with eliminating noises substantially is determined based on the signal generation frequency integrated value distribution. Concretely, first, the preparation of the signal generation frequency integrated value distribution for the pulse signals detected on the time series light intensity data is conducted (step 200). Namely, the number of signals P(I) having an intensity more than the light intensity I in every light intensity I is counted. Then, there is prepared a distribution of the light intensity against square roots of the numbers of signals. P(I) or radial direction distances (radii) r from the maximum intensity point, computed with the square root of the number of signals P(I) using Expression (3) (However, the radius r can be computed only when the light-emitting particle concentration c is known.). (Step 210—see FIG. 6A.). Here, the signal generation frequency integrated value distribution or the distribution of the light intensity I against square roots of the number of signals P(I) or radii r computed therefrom may be displayed on the screen of a display of the computer 18, so that the user of a device can grasp visually easily the signal generation frequency integrated value distribution or the distribution of the light intensity I against square roots of the numbers of signals P(I) or radii r from the maximum intensity point. After this, with reference to the signal generation frequency integrated value distribution or the distribution of the light intensity I against square roots of the numbers of signals P(I) or radii r from the maximum intensity point, the determination of the threshold value for eliminating noise signals and extracting a signal of a light-emitting particle is conducted. For the way of the determination of the threshold value, for example, either of the following ways may be done.

Most easily, the threshold value may be appropriately set from the shape of the distribution by the user of the device seeing the signal generation frequency integrated value distribution or the distribution of the light intensity I against square roots of the numbers of signals P(I) or radii r from the maximum intensity point, displayed on the screen of the display (the judgment of a distribution shape). As already noted, in the distribution of the light intensity I against square roots of the numbers of signals P(I) or radii r from the maximum intensity point or the signal generation frequency integrated value distribution, its shape is bent discontinuously at the boundaries of the intensity range including noises (the upper limit of noise signal intensity) (see FIG. 2E thin solid line). Thus, by specifying a discontinuously bent site on the displayed distribution, the intensity value of the site may be set as the threshold value. To do this, the computer 18 may be so designed that a cursor, etc. can be shown with being superposed on the distribution map on the screen of the display, and the user of the device can move the cursor on the screen to know the light intensity value I and/or the value of the square root of the number of signals P(I) or the radius r of an arbitrary point on the distribution.

For another example of the was for the determination of the threshold value, there is conducted the fitting of the bell shaped function of Expression (5) or (8), Expression (1) or (6) to the distribution of the light intensities I against square roots of the numbers of signals P(I) or radii r from the maximum intensity point, or the fitting of the bell shaped function of Expression (4) or (7) to the signal generation frequency integrated value distribution. Then, it can be judged that a region having a large fitting residual of each light intensity I (fitting error) includes noise area (usually, regions of low light intensity I), and therefore, the light intensity I at the boundary of the region giving the allowable fitting error (corresponding to the upper limit of noise signal intensities) is set as the threshold value. For this process, the fitting of a bell shaped function and calculation of fitting errors may be executed with e.g. the least-squares method by the operation in accordance with a predetermined program in the computer 18. The bell shaped function having been fitted and/or the distribution of fitting errors may be displayed on the screen of the display so that the user of the device can grasp them visually. The boundary of the region giving the allowable fitting error may be determined automatically by the operation in accordance with a predetermined program of the computer 18, or may be appropriately set by the user of the device seeing the distribution of fitting errors on the screen of the display.

For a further alternative example of the ways of the determination of the threshold value, the threshold value may be determined with reference to the slope of the light intensities I to square roots of the numbers of signals P(I) or radii r in the distribution of the light intensities I against square roots of the numbers of signals P(I) or radii r from the maximum intensity point. As understood with reference to the thin solid line in FIG. 2E, in the distribution of the light intensities I against, square roots of the numbers of signals P(I) or radii r from the maximum intensity point, its shape is discontinuously bent at the boundaries of the intensity range including noises, and thus, it can be estimated, with reference to the slope of the light intensities I to square roots of the numbers of signals P(I) or radii r, the light intensity I at the point, whose value discontinuously changes is the upper limit of noise intensities. Accordingly, by computing the slope of the light intensities I to square roots of the numbers of signals P(I) or radii r in this distribution of the light intensities I, the light intensity I of the point whose slope discontinuously changes may be set as the threshold value. In this regard, although not illustrated, the variation of the slope of the light intensities I to square roots of the numbers of signals P(I) or radii r may also be displayed in a graph form on the screen of the display so that the user of the device can set the threshold value appropriately with reference to the displayed graph of the variation of the slope of light intensities I. Further, the threshold value may be automatically determined by the operation in accordance with a predetermined program of the computer 18.

(iii) Extraction of a Signal of a Light-Emitting Particle

Then, when the threshold value for the light intensity I is determined by one of the above-mentioned ways, the signal having the peak intensity more than the above-mentioned determined threshold value among the group of the signals detected from the time series light intensity data by the processes of steps 110-160 is extracted as a signal of a light-emitting particle (step 230), and thereby a single light-emitting particle has been detected individually. In this regard, together with this extracting process, the number of the extracted signals may be counted as the signals of light-emitting particles.

Further, in a case that measurements by the scanning molecule counting method are performed for two or more sample solutions, since it is considered that the conditions of noise generation are substantially the same in the same measurement conditions, a threshold value once determined for a certain sample solution may be used when detecting a signal of a light-emitting particle from time series light intensity data for other sample solutions. In that case, by using the true threshold value determined as noted above, the detection of a signal of a light-emitting particle with eliminating noise signals will be achieved in the signal detection in step 150

(iv) Determination of a Light-Emitting Particle Concentration

The number density or concentration of a light-emitting particle in time series light intensity data can be determined using the number of the signals of the light-emitting particles and the volume of the whole region which the light detection region has passed through during the acquisition of the time series light intensity data. However, the effective volume of the light detection region varies depending on the wavelength of excitation light or detected light, the numerical aperture of lenses and the adjustment condition of the optical system, and therefore, it is generally difficult to compute the effective volume of the light detection region from the design parameter values, and it is not easy to compute the whole volume which the light detection region has passed through, either. Further, as already noted, since the region to be detected in the light detection region changes by the setting of the threshold value, it is difficult to theoretically compute the whole volume of the region. Thus, typically, the light intensity measurement, the detection of particles and the counting thereof are performed as explained above with a solution having a known light-emitting particle concentration (reference solution) under the same condition as that for the measurement of a sample solution to be tested, and then, from the number of detected light-emitting particles and the concentration of the light-emitting particle in the reference solution, the volume of the whole region which the light detection region has passed through, i.e., the relation between the detected number and the concentration of the light-emitting particle, may be determined. Preferably, the light-emitting particle of a reference solution may be a light emitting label (fluorescent dye etc.) having the same wavelength characteristic as the corresponding light-emitting particle. Concretely, for example, supposing the number of detected the light-emitting particles is N in a reference solution of the particle concentration (number density) C, the whole volume Vt of the region to be detected has passed through is given by $$Vt = N/C \tag{13}$$

Alternatively, the plurality of solutions of different concentrations are prepared as reference solutions and the measurement is performed for each of the solutions, and then, the average value of the computed Vt is determined as the whole volume Vt of the region which the area to be detected in the light detection region has passed through. Thus, when Vt is given, the concentration (number density) c of the light-emitting particle of the sample solution, whose counting result of the particles is n, is given by:

$$c = n/Vt \tag{14}$$

In this regard, the volume of the light detection region and the volume of the whole region which the light detection region has passed through may be given by an arbitrary method, for instance, using FCS and FIDA instead of the above-mentioned method. Further, in the optical analysis device of this embodiment, there may be previously memorized in a storage apparatus of the computer 18 the information on the relations (Expression (13)) between concentrations C and particle numbers N of various standard particles for assumed moving patterns of the light detection region, so that a user of the device can appropriately use the memorized information on the relation in conducting an optical analysis.

Thus, according to the above-mentioned present invention, the criterion for detection of a signal of a light-emitting particle with eliminating noise signals from light intensity data in the scanning molecule counting method, i.e., the light intensity range or threshold value for a signal to be extracted as a signal of a light-emitting particle on the time series light intensity data can be efficiently determined based on the signal generation frequency integration value distribution. Thereby, the labor and time which have been required in order to obtain a detected result with eliminating noise signals are reduced, and improvement in the accuracy of detected results is expected.

In order to verify the validity of the present invention explained above, the experiments described below were conducted. In this regard, it should be understood that the following embodiments illustrate the validity of the present invention only, not intended to limit the scope of the present invention.

Embodiment 1

It was verified that a threshold value for eliminating noise signals substantially and detecting a signal of a light-emitting particle from a time series light intensity data obtained in a light measurement by the scanning molecule counting method can be set based on a signal generation frequency integration value distribution.

For sample solutions, there were prepared solutions containing fluorescent dye ATTO633 (Sigma-Aldrich, Cat. No. 18620) as a light-emitting particle at 1 fM, 10 fM and 100 fM in a phosphate buffer (including 0.05% Tween 20), respectively. In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) were acquired for the above-mentioned respective sample solutions in accordance with the manner explained in the above-mentioned "(2) Measurement of Light Intensity of a Sample Solution". In that time, a 633-nm laser light was used for excitation light, and, using a band pass filter, the light of the wavelength bands, 660 to 710 nm, was measured, and time series light intensity data was generated. The position of the light detection region in the sample solution was moved at the moving speed of 22.5 mm/second; BIN TIME was set to 10 μseconds and measurements for 20 seconds were performed for the respective solutions. After the light intensity measurement, in accordance with the procedures described in the above-mentioned "(3)(i) Detection of a Signal on Time Series Light Intensity Data", the smoothing treatment was applied to the time series light intensity data acquired for the respective sample solutions, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined.

And, only the pulse signals satisfying the following conditions:

20 μsec.<pulse width<400 μsec.

Peak intensity>1 [pc/10 μsec.]

Correlation coefficient>0.95     (A)

were extracted. Subsequently, the number of signals having an intensity beyond the light intensity I for every light intensity I is counted (preparation of a signal generation frequency integrated value distribution), and then a distribution of the light, intensities I against square roots of the numbers of signals was prepared, and further, the fitting of Expression (8) was conducted to the distribution of the light intensities I against square roots of the numbers of signals.

FIG. 6A shows a distribution of the light intensities I against square roots of the numbers of signals prepared from time series light intensity data obtained for the sample solution of the light-emitting particle concentration of 1 fM and the fitting curve. In the drawing, the actual data are in only the right half, and the left half is plots prepared for the fitting by reversing the signs of the square roots of the numbers of signals in the right half data. In this regard, because of smoothing the photon count data, the indication below a decimal point appears in the photon count. Namely, the photon count value is treated as a continuous value by the smoothing treatment.

Referring to this drawing, as expected from the explanation in conjunction with FIG. 2E, the plots of the light intensities I corresponded with the fitting curve well in the light intensity I of about two or more, and the plots of the light, intensities I deviated from the fitting curve and was expanded outwardly in the light intensity I of less than about 2. This suggest that noise signals were included in the light intensity range where the light intensity I was lower than about 2. Also, as shown in FIG. 6B, for the fitting errors, there was prepared a distribution of square values (square values of residuals) of the differences between the plots of the light intensities I of FIG. 6A against square roots of the numbers of signals and the fitting curve (a light intensity I of a plot the light intensity I of the fitting curve). Then, in the drawing, the square root of the numbers of signals giving a fitting error of 1 or less was 3.16, and the light intensity I for the square root of the number of signals=3.16 was 2 in FIG. 6A. Thus, in the time series light intensity data of FIG. 6A, the upper limit of noise signals was 2, and when the signal of a light-emitting particle is extracted by using this value as the threshold value, the results in which noise signals have been eliminated will be obtained.

FIG. 7A is a figure in which the numbers of signals of the light-emitting particles extracted with setting 2 for the threshold value from the time series light intensity data acquired for each sample solution are plotted against, each concentration. As understood from this drawing, the number of signals of light-emitting particles increased in proportion to the light-emitting particle concentration in the sample solution, and agreed well with approximate straight line, obtained by the least-squares method, of the numbers of signals of the light-emitting particles against concentrations (Correlation coefficient $R^2$ was 0.9624.).

Furthermore, in order to verify the validity of the threshold value set in the above, after counting the number of the signals extracted from time series light intensity data with changing the threshold value variously for each sample solutions, the straight line approximation to the numbers of signals of the light-emitting particles by the least-squares method was performed for each concentration, and the slopes and correlation coefficients $R^2$ of the approximate lines were computed. FIG. 7B is the drawing in which the slopes and correlation coefficients $R^2$ of the approximate lines are plotted against threshold values. Referring to this drawing, the correlation coefficient $R^2$ was small in a small threshold value, and saturated around 0.9 in two or more of the threshold value. This suggests that the ratio of noise signals in the number of signals extracted from time series light intensity data is higher as the threshold value is smaller, and the noise signals have been substantially eliminated at the threshold value of two or more. Further, as for the slope of the approximate line, this value reduced as the threshold value increased. This is because, when the threshold value increases, the region to be detected in the light detection region contracts so that the detected number of signals of light-emitting particles will be reduced. In detecting the number of signals of light-emitting particles for a concentration, the accuracy of the ratio of the number of signals of light-emitting particles to a concentration improves as the numbers of signals of light-emitting particle is larger. Therefore, in the present embodiment, it can be said that 2 with which the correlation coefficient value $R^2$ begins to be saturated, is optimum as the threshold value.

Thus, as understood from the results of the above-mentioned embodiment, has been shown that, in accordance with teachings of the above-mentioned present invention, the threshold value which is a criterion for detection of a signal of a light-emitting particle in the scanning molecule counting method can be set efficiently using the signal generation frequency integrated value distribution. According to the present invention, trial and error for the setting of a threshold value, namely, the operation process of repeating detection of a signal of a light-emitting particle with changing a threshold value variously becomes unnecessary, and accordingly, it is expected that the labor and time of data processing in the scanning molecule counting method will be reduced, and the accuracy of the result will be improved. And thereby, the expansion of the use range of the scanning molecule counting method is expected, also.

The invention claimed is:

1. An optical analysis device which detects light from a light-emitting particle dispersed and moving at random in a sample solution using an optical system of a confocal microscope or a multiphoton microscope, comprising:
   a light detection region mover which moves a position of a light detection region of the optical system in the sample solution by changing an optical path of the optical system;
   a light detector which detects light from the light detection region; and
   a signal processor which generates time series light intensity data of the light from the light detection region detected with the light detector while moving the position of the light detection region in the sample solution and which detects a signal from each light-emitting particle individually in the time series light intensity data;
   wherein the signal processor detects the signal from each light-emitting particle by extracting a signal having a light intensity in a light intensity range having been set based upon a signal generation frequency integrated value distribution as the signal of the light-emitting particle from a group of signals detected in the time series light intensity data;
   wherein the signal generation frequency integrated value distribution is a distribution of integrated values of generation frequencies of signals having an intensity not lower than a variable; and
   wherein the variable is an intensity of a signal detected in the time series light intensity data.

2. The device of claim 1,
   wherein the signal processor extracts a signal having an intensity beyond a threshold value as the signal of the light-emitting particle, and
   wherein the threshold value is determined based on the signal generation frequency integrated value distribution of the time series light intensity data.

3. The device of claim 1,
   wherein the light intensity range set based on the signal generation frequency integrated value distribution is a light intensity range in which an intensity distribution of signals against positions in the light detection region substantially accords with an intensity distribution of lights emitted from light-emitting particles in the light detection region and detected with the light detector, and
   wherein the intensity distribution of signals against positions in the light detection region is determined based on the signal generation frequency integrated value distribution.

4. The device of claim 1, wherein the signal processor can determine an upper limit of noise intensities in the time series light intensity data based on the signal generation frequency integrated value distribution.

5. The device of claim 1,
   wherein the signal processor has a display which can display a distribution of intensities of the signals against function values of positions in the light detection region and/or the signal generation frequency integrated value distribution, and
   wherein the distribution of intensities of signals against function values of positions in the light detection region is determined based on the signal generation frequency integrated value distribution.

6. The device of claim 5,
   wherein a user of the device can set the light intensity range for the signal to be extracted as the signal of the light-emitting particle of the time series light intensity data on the distribution of intensities of the signals against function values of positions in the light detection region and/or on the signal generation frequency integrated value distribution, displayed on the display.

7. The device of claim 1,
   wherein the light intensity range for the signal to be extracted as the signal of the light-emitting particle of the time series light intensity data is settable based on a fitting error in a fitting of a bell shaped function to a distribution of intensities of signals against function values of positions in the light detection region, and
   wherein the distribution of intensities of signals is determined based on the signal generation frequency integrated value distribution.

8. The device of claim 1,
   wherein the light intensity range for the signal to be extracted as the signal of the light-emitting particle of the time series light intensity data is settable based on a shape of a distribution of intensities of signals against function values of positions in the light detection region, and
   wherein the distribution of intensities of signals is determined based on the signal generation frequency integrated value distribution, or based on a shape of the signal generation frequency integrated value distribution.

9. The device of claim 1,
   wherein the light intensity range for the signal to be extracted as the signal of the light-emitting particle of the time series light intensity data is settable based on a slope of intensities of signals to function values of positions in the light detection region in a distribution of intensities of signals against function values of positions in the light detection region, and wherein the distribution of intensities of signals is determined based on the signal generation frequency integrated value distribution.

10. The device of claim 1, wherein the light detection region mover moves the position of the light detection region at velocity quicker than a diffusion moving velocity of the light-emitting particle.

11. The device of claim 1, wherein the signal processor determines a number density or concentration of the light-emitting particle in the sample solution based on the number of the detected light-emitting particles.

12. An optical analysis method of detecting light from a light-emitting particle dispersed and moving at random in a sample solution using an optical system of a confocal microscope or a multiphoton microscope, comprising:

(a) moving a position of a light detection region of the optical system in the sample solution by changing an optical path of the optical system;

(b) detecting intensity of light from the light detection region while moving the position of the light detection region in the sample solution and generating time series light intensity data; and (c) detecting a signal indicating light from the light-emitting particle individually on the time series light intensity data, wherein, in the step (c), the signal from each light-emitting particle is detected by extracting a signal having a light intensity in a light intensity range having been set based upon a signal generation frequency integrated value distribution as the signal of the light-emitting particle from a group of signals detected in the time series light intensity data;

wherein the signal generation frequency integrated value distribution is a distribution of integrated values of generation frequencies of signals having an intensity not lower than a variable; and wherein the variable is a signal detected in the time series light intensity data.

13. The method of claim 12, wherein, in the step (c), a signal having an intensity beyond a threshold value is extracted as the signal of the light-emitting particle, and wherein the threshold value is determined based on the signal generation frequency integrated value distribution.

14. The method of claim 12, wherein the light intensity range set based on the signal generation frequency integrated value distribution is a light intensity range in which an intensity distribution of signals against positions in the light detection region substantially accords with an intensity distribution of lights emitted from light-emitting particles in the light detection region and detected with the light detector, wherein the intensity distribution of signals against positions in the light detection region is determined based on the signal generation frequency integrated value distribution.

15. The method of claim 12, wherein, in the step (c), an upper limit of noise intensities in the time series light intensity data is determined based on the signal generation frequency integrated value distribution.

16. The method of claim 12, wherein, in the step (c), the light intensity range for the signal to be extracted as the signal of the light-emitting particle of the time series light intensity data is set on the distribution of intensities of the signals against function values of positions in the light detection region and/or on the signal generation frequency integrated value distribution, displayed on a display.

17. The method of claim 12, wherein, in the step (c), the light intensity range for the signal to be extracted as the signal of the light-emitting particle of the time series light intensity data is set based on a fitting error in a fitting of a bell shaped function to a distribution of intensities of signals against function values of positions in the light detection region, and wherein the distribution of intensities of signals is determined based on the signal generation frequency integrated value distribution.

18. The method of claim 12, wherein, in the step (c), the light intensity range for the signal to be extracted as the signal of the light-emitting particle of the time series light intensity data is set based on a shape of a distribution of intensities of signals against function values of positions in the light detection region, determined based on the signal generation frequency integrated value distribution, or based on a shape of the signal generation frequency integrated value distribution, and wherein the distribution of intensities of signals is determined based on the signal generation frequency integrated value distribution.

19. The method of claim 12, wherein, in the step (c), the light intensity range for the signal to be extracted as the signal of the light-emitting particle of the time series light intensity data is set based on a slope of intensities of signals to function values of positions in the light detection region in a distribution of intensities of signals against function values of positions in the light detection region, and wherein a distribution of intensities of signals is determined based on the signal generation frequency integrated value distribution.

20. The method of claim 12, wherein the position of the light detection region is moved at velocity quicker than a diffusion moving velocity of the light-emitting particle.

21. The method of claim 12, further comprising a step of (d) determining a number density or concentration of the light-emitting particle based on the number of the detected light-emitting particles.

* * * * *